US00PP15451P2

(12) United States Plant Patent
Osiecki

(10) Patent No.: US PP15,451 P2
(45) Date of Patent: Dec. 21, 2004

(54) ***SPATHIPHYLLUM* PLANT NAMED 'POWER PLANT'**

(50) Latin Name: *Spathiphyllum hybrid*
Varietal Denomination: Power Plant

(75) Inventor: Marian Wincenty Osiecki, Marianna, FL (US)

(73) Assignee: Oglesby Plants International, Inc., Altha, FL (US)

( * ) Notice: Subject to any disclaimer, the term of this patent is extended or adjusted under 35 U.S.C. 154(b) by 0 days.

(21) Appl. No.: 10/287,076

(22) Filed: Nov. 4, 2002

(51) Int. Cl.[7] ..... A01H 5/00
(52) U.S. Cl. ..... Plt./364
(58) Field of Search ..... Plt./364

*Primary Examiner*—Anne Marie Grunberg
*Assistant Examiner*—June Hwu
(74) *Attorney, Agent, or Firm*—C. A. Whealy

(57) ABSTRACT

A distinct cultivar of *Spathiphyllum* plant named 'Power Plant', characterized by its compact, symmetrical, bushy, upright and somewhat outwardly arching plant habit; relatively small stature, suitable for 15-cm containers; vigorous and freely clumping growth habit; glossy and dark green leaves; very early and freely flowering habit; white-colored spathes that are positioned above the foliage on strong and erect peduncles; and good postproduction longevity.

1 Drawing Sheet

Botanical classification/cultivar designation: *Spathiphyllum hybrid* cultivar Power Plant.

BACKGROUND OF THE INVENTION

The present Invention relates to a new and distinct cultivar of *Spathiphyllum* plant, botanically known as *Spathiphyllum hybrid* , and hereinafter referred to by the cultivar name Power Plant.

The new cultivar is a product of a planned and controlled breeding program conducted by the Inventor in Altha, Fla. The objective of the breeding program is to create new compact and vigorous *Spathiphyllum* cultivars with dark green foliage and freely flowering habit.

The new cultivar originated from a cross-pollination made by the Inventor in July, 1994 of the *Spathiphyllum* hybrid cultivar S8, disclosed in U.S. Plant Pat. No. 9,677, as the female or seed parent and a proprietary *Spathiphyllum* hybrid seedling selection identified as code number 91-FF-1, not patented, as the male or pollen parent. The cultivar Power Plant was discovered and selected by the Inventor as a single plant within the progeny of the stated cross-pollination in a controlled environment in Altha, Fla., in July, 1995.

Asexual propagation of the new cultivar by tissue culture since October, 1998, in a laboratory in Altha, Fla., has shown that the unique features of this new *Spathiphyllum* plant are stable and reproduced true to type in successive generations of asexual propagation.

SUMMARY OF THE INVENTION

The new *Spathiphyllum* has not been observed under all possible environmental conditions. The phenotype may vary somewhat with variations in environment such as temperature and light intensity without, however, any variance in genotype.

The following traits have been repeatedly observed and are determined to be the unique characteristics of 'Power Plant'. These characteristics in combination distinguish 'Power Plant' as a new and distinct *Spathiphyllum* cultivar:

1. Compact, symmetrical, bushy, upright and somewhat outwardly arching plant habit; relatively small stature, suitable for 15-cm containers.
2. Vigorous and freely clumping growth habit.
3. Glossy and dark green leaves.
4. Very early and freely flowering habit.
5. White-colored spathes that are positioned above the foliage on strong and erect peduncles.
6. Good postproduction longevity.

Plants of the new *Spathiphyllum* can be compared to plants of the female parent, the cultivar S8. In side-by-side comparisons conducted in Altha, Fla., plants of the new *Spathiphyllum* differed from plants of the cultivar S8 in the following characteristics:

1. Plants of the new *Spathiphyllum* were smaller and more compact than plants of the cultivar S8.
2. Plants of the new *Spathiphyllum* had a more vigorous and freely clumping growth habit than plants of the cultivar S8.
3. Plants of the new *Spathiphyllum* flowered earlier and were more freely flowering than plants of the cultivar S8.
4. Leaves of plants of the new *Spathiphyllum* were smaller and had shorter petioles than leaves of plants of the cultivar S8.
5. Spathes of plants of the new *Spathiphyllum* were smaller and were positioned closer to the foliage than spathes of plants of the cultivar S8.

Plants of the new *Spathiphyllum* can be compared to plants of the male parent, the selection 91-FF-1. In side-by-side comparisons conducted in Altha, Fla., plants of the new *Spathiphyllum* differed from plants of the selection 91-FF-1 in the following characteristics:

1. Plants of the new *Spathiphyllum* were smaller, more compact and more upright than plants of the selection 91-FF-1.
2. Plants of the new *Spathiphyllum* had a more vigorous and freely clumping growth habit than plants of the selection 91-FF-1.

3. Plants of the new *Spathiphyllum* flowered earlier and were more freely flowering than plants of the selection 91-FF-1.
4. Leaves of plants of the new *Spathiphyllum* were smaller and thinner than leaves of plants of the selection 91-FF-1.
5. Spathes of plants of the new *Spathiphyllum* were smaller than spathes of plants of the selection 91-FF-1.

Plants of the new *Spathiphyllum* can be compared to plants of the *Spathiphyllum* cultivar Petite, not patented. However, in side-by-side comparisons conducted in Altha, Fla., plants of the new *Spathiphyllum* differed from plants of the cultivar Petite in the following characteristics:

1. Plants of the new *Spathiphyllum* were more compact and bushier than plants of the cultivar Petite.
2. Plants of the new *Spathiphyllum* had a more vigorous and freely clumping growth habit than plants of the cultivar Petite.
3. Plants of the new *Spathiphyllum* flowered much earlier and were more freely flowering than plants of the cultivar Petite.
4. Leaves of plants of the new *Spathiphyllum* were larger, darker green and glossier than leaves of plants of the cultivar Petite.
5. Plants of the new *Spathiphyllum* flowered year round whereas plants of the cultivar Petite only flowered during the spring and fall.
6. Spathes of plants of the new *Spathiphyllum* were positioned closer to the foliage on shorter peduncles than spathes of plants of the cultivar Petite.

Plants of the new *Spathiphyllum* can also be compared to plants of the *Spathiphyllum* cultivar S4, disclosed in U.S. Plant Pat. No. 10,013. However, in side-by-side comparisons conducted in Altha, Fla., plants of the new *Spathiphyllum* differed from plants of the cultivar S4 in the following characteristics:

1. Plants of the new *Spathiphyllum* were smaller, more compact and bushier than plants of the cultivar S4.
2. Plants of the new *Spathiphyllum* had a more vigorous and freely clumping growth habit than plants of the cultivar S4.
3. Plants of the new *Spathiphyllum* flowered earlier and were more freely flowering than plants of the cultivar S4.
4. Leaves of plants of the new *Spathiphyllum* were broader, darker green and glossier than leaves of plants of the cultivar S4.
5. Spathes of plants of the new *Spathiphyllum* were positioned closer to the foliage on stronger and shorter peduncles than spathes of plants of the cultivar S4.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Spathiphyllum*.

The photograph at the top of the first sheet comprises a side perspective view of a typical plant of 'Power Plant' grown in a 15-cm container.

The photograph at the bottom of the sheet comprises a close-up view of typical inflorescences and leaves of 'Power Plant'.

DETAILED BOTANICAL DESCRIPTION

The aforementioned photographs and following observations and measurements describe 56-week old plants (from planting rooted tissue-cultured plantlets) grown in Altha, Fla., in a polycarbonate-covered greenhouse and under commercial production conditions in 15-cm containers with a single plantlet per container. During the production of the plants, day temperatures ranged from 24 to 32° C., night temperatures ranged from 22 to 25° C. and light levels were about 800 to 1,200 foot-candles.

In the following description, color references are made to The Royal Horticultural Society Colour Chart, 1995 Edition, except where general terms of ordinary dictionary significance are used.

Botanical classification: *Spathiphyllum* hybrid cultivar Power Plant.

Parentage:

*Female parent.*—*Spathiphyllum* hybrid cultivar S8, disclosed in U.S. Plant Pat. No. 9,677.

*Male parent.*—Proprietary *Spathiphyllum* hybrid seedling selection identified as code number 91-FF-1, not patented.

Propagation:

*Type.*—By tissue culture.

*Time to initiate roots on a tissue-cultured cutting.*—Summer: About 18 to 21 days at 25 to 30° C. soil temperature. Winter: About 24 to 28 days at 22 to 27° C. soil temperature.

*Time to produce a fully-rooted tissue-cultured plantlet.*—Summer: About 98 days at 25 to 30° C. soil temperature. Winter: About 112 days at 22 to 27° C. soil temperature.

*Root description.*—Primary roots, very thick and fleshy; lateral branch roots, fine; primary and lateral roots white in color and numerous.

Plant description:

*Plant shape.*—Compact, upright, somewhat outwardly arching and symmetrical plant habit; relatively small stature, plants of the new *Spathiphyllum* are typically grown in 15-cm containers.

*Growth habit.*—Erect when young, becoming outwardly arching as leaves develop. Freely clumping and bushy full appearance; about 11 clumps per plant. Vigorous growth habit and rapid growth rate; from tissue-cultured plantlets, about 13 months are required to produce finished flowering plants in 15-cm containers.

*Plant height.*—About 28 cm from soil level to top of leaf plane and about 48 cm from soil level to spathe apices.

*Plant spread.*—About 51 cm.

*Foliage description.*—Length: About 20 cm. Width: About 9 cm. Shape: Ovate. Apex: Acuminate, elongated. Base: Obtuse. Margin: Entire; undulate. Aspect: Initially upright, then outwardly arching; leaves curved downward towards the apex. Surface: Midrib and lateral veins sunken on upper surface and prominent on lower surface; upper surface of blade convex between veins, lower surface of blade concave between veins; upper and lower surfaces rugose. Texture, upper and lower surfaces: Leathery, smooth, glabrous, durable and flexible. Luster, upper and lower surfaces: Glossy; young leaves glossier than fully expanded leaves. Venation pattern: Pinnate; about 15 pairs of primary veins per leaf. Color: Young leaves, upper surface: More green than 147A. Young leaves, lower surface: Close to 147B. Fully expanded leaves, upper surface: Darker than 147A. Fully expanded leaves, lower surface: Close to 147B. Midvein and lateral veins, upper surface: Darker than 147A. Midvein, lower surface: 144A. Lateral veins, lower surface: Close to 146D. Petiole: Length: About 17 cm. Diameter, just below the geniculum: About 4 mm. Petiole sheath, length: About 13.5 cm. Petiole sheath, width at midpoint, unfurled: About 5 mm. Petiole sheath, apex: Rounded. Geniculum length: About 7 mm. Geniculum diameter: About 5 mm. Geniculum aspect: Straight to slightly curved. Color: Petiole: 147A. Petiole sheath: 147A. Geniculum: Darker than 144A.

Inflorescence description:

*Inflorescence arrangement/quantity*.—Concave spathes with spadices held above the foliage on strong and erect peduncles. Freely flowering; typically at least five developing and open spathes per plant at one time; inflorescences arise from the petiole sheath.

*Time to flower*.—Plants start flowering about 22 weeks after planting rooted tissue-cultured plantlets.

*Inflorescence longevity*.—Spathes generally maintain white color for about 4 weeks on the plant becoming eventually entirely green with subsequent development. As cut flowers, spathes maintain good substance for about one to two weeks.

*Fragrance*.—Fragrant, sweet and spicy, typical of *Spathiphyllum*.

*Inflorescence buds*.—Length: About 7 cm. Diameter, widest point: About 6 mm. Shape: Columnar. Color: Close to 155A.

*Spathe*.—Length: About 12.5 cm. Width: About 7 cm. Depth: About 1.4 cm. Shape: Ovate. Apex: Acuminate, elongated; twisted. Base: Obtuse to oblique. Aspect: Concave. Color: Front and back surfaces: Close to 155D; midrib, close to 144A. Front and back surfaces with subsequent development: More green than 144A; midrib, more green than 144A.

*Spadix*.—Length: About 5.3 cm. Diameter: About 1.4 cm. Color: Close to 158A gradually becoming more green than 146A with subsequent development. Quantity of flowers per spadix: About 105. Stamens: Anthers and filaments minute. Pollen: Moderate. Pollen color: Close to 158A. Pistils: Conical; pistillate flowers extend about 3 mm beyond the staminate flowers; close to 158A in color.

*Peduncle*.—Length: About 31 cm. Diameter, at midpoint: About 4 mm. Aspect: Straight, erect. Color: More green than 146A.

*Fruit/seed*.—Fruit and seed production have not been observed.

Disease/pest resistance: Plants of the new *Spathiphyllum* have not been observed to be resistant to pathogens or pests common to *Spathiphyllum*.

It is claimed:

1. A new and distinct cultivar of *Spathiphyllum* plant named 'Power Plant', as illustrated and described.

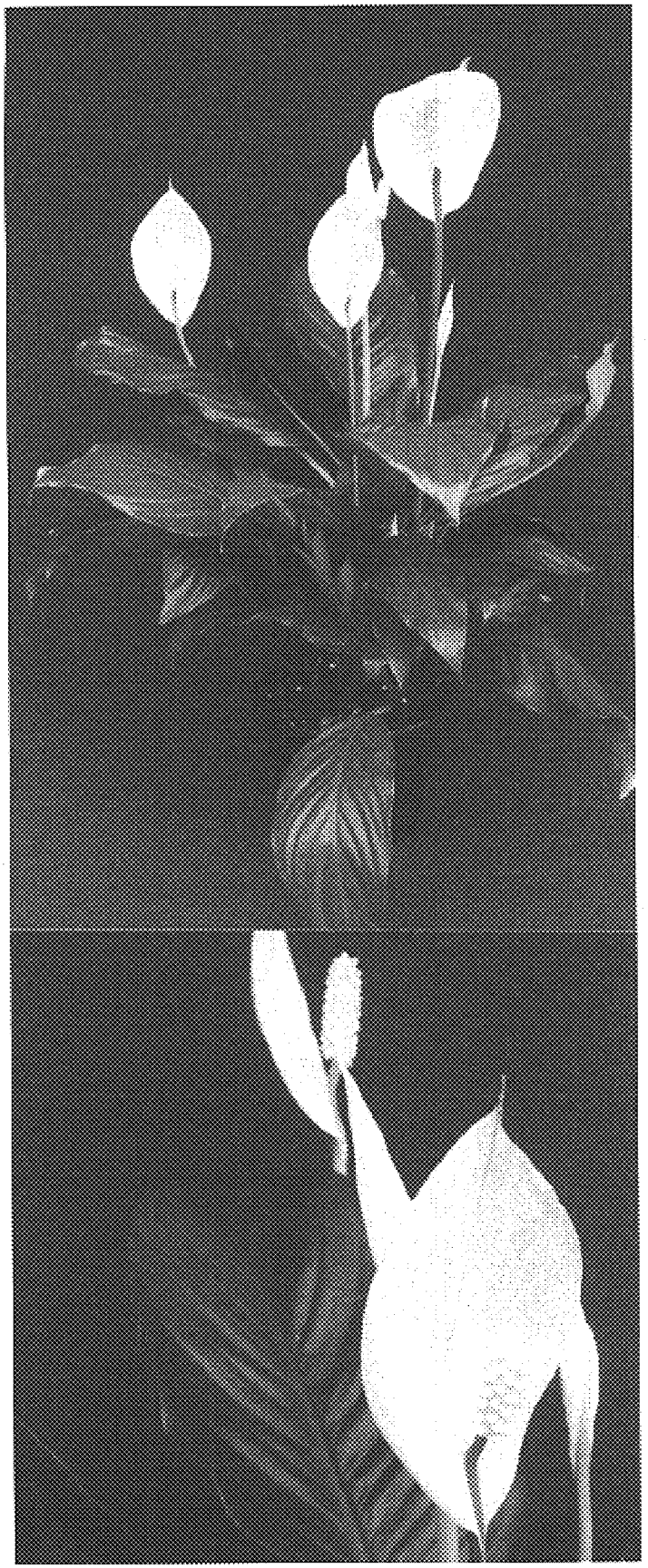

* * * * *